United States Patent [19]
Kirkpatrick

[11] Patent Number: 5,932,251
[45] Date of Patent: Aug. 3, 1999

[54] HAIR GROWTH PROMOTER AND METHOD OF USING SAME

[76] Inventor: Carole M. Kirkpatrick, R.R. 2, Box 214, Beecher City, Ill. 62414

[21] Appl. No.: 09/063,479

[22] Filed: Apr. 20, 1998

Related U.S. Application Data

[60] Provisional application No. 60/043,973, Apr. 23, 1997.

[51] Int. Cl.[6] .......................... A61K 33/34; A61K 33/24; A61K 33/38; A61K 7/06
[52] U.S. Cl. .......................... 424/618; 424/630; 424/649; 424/70.1; 514/880; 514/881
[58] Field of Search .................... 424/618, 630, 424/649, 70.1; 514/880, 881

[56] References Cited

U.S. PATENT DOCUMENTS

| | | | |
|---|---|---|---|
| 4,960,588 | 10/1990 | Hoshowski et al. | 424/70.122 |
| 5,340,579 | 8/1994 | Casero | 424/114 |
| 5,472,688 | 12/1995 | Soukup | 424/70.1 |
| 5,472,697 | 12/1995 | Hirano et al. | 424/401 |
| 5,494,667 | 2/1996 | Uchida et al. | 424/195.1 |
| 5,538,945 | 7/1996 | Pallenberg et al. | 514/6 |
| 5,550,183 | 8/1996 | Pickart | 514/6 |
| 5,674,497 | 10/1997 | Kuwana et al. | 424/195.1 |
| 5,674,510 | 10/1997 | DiTucci | 424/401 |
| 5,676,957 | 10/1997 | Nakamura et al. | 424/401 |
| 5,679,378 | 10/1997 | Fischer | 424/600 |
| 5,681,554 | 10/1997 | Cannell et al. | 424/70.14 |

*Primary Examiner*—John Pak
*Attorney, Agent, or Firm*—Grace J. Fishel

[57] ABSTRACT

A hair growth promoter capable of acting as a cosmetic, reducing alopecia, eliminating alopecia, increasing hair growth or any combination thereof is disclosed. The hair growth promoter comprises a colloidal silver, copper and gold complex in a cosmetically acceptable carrier, formed from silver, copper and gold colloids made electrically. The promoter is applied to a treatment area in an amount sufficient to wet the scalp at least one time a week.

3 Claims, No Drawings

HAIR GROWTH PROMOTER AND METHOD OF USING SAME

This application claims the benefit of prior U.S. provisional application Ser. No. 60/043,973, filed Apr. 23, 1997.

BACKGROUND OF THE INVENTION

1. Field of the Invention

The present invention relates to a hair growth promoter containing a colloidal silver, copper and gold complex in a cosmetically acceptable carrier formed from a mixture of silver, copper and gold colloids made electrically. The promoter is capable of acting as a cosmetic, reducing alopecia, eliminating alopecia, stimulating hair growth or any combination thereof.

2. Brief Description of the Prior Art

Hair loss is a common problem, in both men and women, the most common form being androgenetic alopecia (AGA) where males lose scalp hair as they get older (i.e., male pattern baldness). Other hair loss afflictions include alopecia arcata (AA), female pattern baldness and hair loss secondary to chemotherapy and/or radiation treatment (i.e., secondary alopecia). Although the only physical effect of hair loss is cosmetic, the psychological effects can be devastating and the pressure to find an effective treatment is intense.

A variety of procedures and drugs have been utilized in an attempt to treat hair loss. A common technique includes hair transplantation. Briefly, plugs of skin containing hair are transplanted from areas of the scalp where hair is growing to bald or balding areas of the scalp. This procedure, however, is time-consuming and relatively painful. Other approaches include ultraviolet radiation and exercise therapy.

More recently, drug therapy has been used to stimulate hair growth. One of the most well-recognized hair-growth agents is sold under the trademark "Rogaine." While systemic treatment with Rogaine stimulates hair-growth in some people, regrowth does not occur in all people and, in some subjects, there are adverse side effects, such as stimulating the growth of facial hair in female patients. A localized, topical treatment, which has a stimulatory effect on hair growth or which improves scalp tone would be preferred, as the number of negative side effects likely would be fewer than with a systemic treatment.

SUMMARY OF THE INVENTION

In view of the above, it is an object of the present invention to provide a hair growth promoter which can be topically applied to the scalp for reducing alopecia, eliminating alopecia, stimulating hair growth or any combination thereof. It is another object to provide a hair growth promoter which is effective for the above-mentioned purposes and can be applied topically without any known negative side effects. A further object is to provide a hair growth promoter that reduces dandruff and itching of the scalp and makes the hair appear thicker, fuller and more manageable. Other objects and features of the invention will be in part apparent and in part pointed out hereinafter.

In accordance with the invention, a hair growth promoter capable of acting as a cosmetic, reducing alopecia, eliminating alopecia, stimulating hair growth or any combination thereof contains a colloidal silver, copper and gold complex in a cosmetically acceptable carrier. The complex is preferably formed by blending colloidal silver, colloidal copper and colloidal gold microclusters formed electrically by passing an electrical current through water, preferably distilled, magnetized water, between silver, copper and gold electrodes, respectively. The complex preferably contains 50 to 70% by volume silver colloid, 20 to 30% by volume copper and 10% by volume gold.

A method for reducing alopecia comprises applying topically to the scalp of a person having a treatment area in need thereof an effective amount of the hair growth promoter. The method includes the step of contacting the hair growth promoter with the treatment area so that alopecia is reduced. Preferably enough promoter should be applied to the treatment area to wet the scalp at least once a week.

The invention summarized above comprises the compositions and methods hereinafter described, the scope of the invention being indicated by the subjoined claims.

DETAILED DESCRIPTION OF THE INVENTION

A hair growth promoter containing a colloidal silver, copper and gold complex in accordance with the present invention is capable of acting as a cosmetic, reducing alopecia, eliminating alopecia, increasing hair growth or any combination thereof. The hair growth promoter is also capable of reducing dandruff and itching of the scalp and making the hair appear thicker, fuller and more manageable.

As used in this application, "negative side effects" refers to side effects which are harmful or undesirable to the subject of the treatment. Such side effects, include but are not limited to, a dry scalp, a burning scalp or a rash. A "cosmetic" means a composition of matter which can provide improved qualities to skin. "Treatment area" is an area to which the hair growth promoter is applied. Such an area typically includes an, at least partially, bald human head. By "reducing alopecia" is meant a noticeable decrease in hair loss over a period of several weeks. "Eliminating alopecia" denotes no noticeable hair loss over several weeks. "Increasing hair growth" refers to a visually discernable increase in hair growth over several weeks, typically starting with very fine, white hairs and eventually proceeding to thicker, colored hair.

A colloidal silver, copper and gold complex for use as a hair growth promoter is formed from a mixture of silver, copper and gold colloids, each of which is made electrically by passing an electrical current through water between silver, copper and gold electrodes, respectively. Colloids made in this manner, for the present purpose, are believed to be superior to those which may be made chemically for various industrial purposes.

The electrodes are made from pure or near-pure metal and are spaced apart and partially immersed in water in a non-conductive, non-reactive vessel. For the silver electrodes, 0.999 fine silver, is preferred, either as #10 or #12 gauge wire or as #18 or #22 gauge strips. Similar considerations are involved in the selection of the material for the copper and gold electrodes. The vessel is preferably formed of glass and the water must be distilled and is preferably magnetized prior to starting current flowing through the system. A positive electrical charge is connected to one of the electrodes and a negative charge to the other. As a current flows from one electrode, through the water to the other electrode, particles of metal from the electrodes are blown off. The fine metal dust dislodged by the current consists of microclusters of atoms and forms the colloidal form of the metal. For a better grade of the colloid, it is preferred that the voltage be between 5 and 12 volts and that the amperage be between 1 and 6 amps. Suitable equipment for making colloidal silver is described in *How to Make Colloids at*

*Home* published by The Heritage Institute, a copy of which was filed in the provisional application and is incorporated by reference herein. Colloidal copper and colloidal gold can be produced with the same equipment by replacing the silver electrodes with copper and gold electrodes, respectively.

A therapeutically active complex is formed by blending colloidal silver, copper and gold solutions. Any amount of colloidal silver, colloidal copper and colloidal gold may be included in the complex so long as the mixture is capable of acting as a cosmetic, reducing alopecia, eliminating alopecia, increasing hair growth or any combination thereof. Preferably the therapeutic complex for cosmetic application contains more silver colloid than copper and more copper colloid than gold. Especially good results have been obtained when the colloidal complex contains 50 to 70% by volume silver colloid, 30 to 40% by volume copper colloid and 10% by volume gold colloid.

The hair growth promoter containing a colloidal silver, copper and gold complex in accordance with the present invention is preferably administered in a cosmetically acceptable carrier, which may be water when the product is administered as a spray. The carrier may include essential oils and an emulsifier such as lecithin. Any amount of carrier may be used so long as the product is capable of acting as a cosmetic, reducing alopecia, eliminating alopecia, increasing hair growth or any combination thereof. It will also be understood that the hair growth promoter can be formulated in various forms such as a liquid, cream, ointment, gel, aerosol, etc. The product can take the form of a hair cream, hair tonic, hair lotion, hair mousse, hair gel, hair spray, hair shampoo, hair rinse and so forth. In a preferred form, the hair growth promoter comprises 50% by volume of a complex of silver, copper and gold colloids, made electrically as described above, and 50% by volume water, preferably magnetized, containing essential oils and lecithin.

Methods of applying the hair growth promoter are limited only in that it should be allowed to reduce alopecia, eliminate alopecia, increase hair growth, act as a cosmetic or any combination thereof. Typically, the promoter is applied in a water carrier as a spray directly to the treatment area. It is believed that optimal results are achieved when the hair treatment promoter is applied directly to the treatment area, in discrete applications, twice to three times a day in an amount sufficient to wet the scalp. While some benefit may be noticed in a few days, the treatment should be carried out for at least about two months. When the treatment area is a bald spot, it has been found that new hair growth starts along the hairline bordering the spot, gradually filling it in. If the subject has been bald for a long time or if the bald spot is very shiny, it may take longer than two months to initiate hair growth. For maintenance of hair growth and hair condition, a single application once a week will be sufficient in many instances.

While certain treatment conditions have been disclosed herein, it is to be understood that other treatment conditions may also provide the desired properties of the present invention.

EXAMPLE 1

Using a low voltage unit as shown and described in "How to Make Colloids at Home," a colloidal complex of silver was made with silver electrodes, operated at 12 volts, 1 amp. Prior to starting current flow, the electrodes were partially immersed in distilled, magnetized water. To make a gallon took about 12–14 hours, while a quart took about 3–6 hours. A colloidal complex of copper was made with copper electrodes and a colloidal complex of gold was made with gold electrodes under similar conditions.

Each of the colloidal complexes were strained twice through 4 to 5 thicknesses of unbleached coffee filters and then the three were blended together in the following ratio by volume: 70% silver, 20% copper and 10% gold.

To make 1 oz of hair growth promoter, ½ oz of the colloidal complex was mixed with ½ oz of distilled water which had been magnetized to which ¼ teaspoon of lecithin granules had been added together with one drop of each of the following essential oils, commercially available from a number of different sources: lavender, patchouli, spruce, myrrh and frankincense. Colorants such as #1 blue may be added, if desired.

EXAMPLE 2

The hair growth promoter formed as described in Example 1 was applied to the scalp of an 85 year old female with female pattern baldness. The promoter was applied heavily on the first application to the point of running off the scalp. Thereafter, the promoter was applied twice a day, morning and night, for one week. For these applications, the promoter was misted on the scalp with a spray pump in an amount sufficient to dampen the scalp but with no run off. Within about three days, the hair began to fill in the bald areas. After the end of the first week, the subject continued to apply the promoter once a week with continued hair growth and no negative side effects.

EXAMPLE 3

A hair growth promoter as in Example 1 was applied to the scalp of a 40 year old man with male pattern baldness with an absence of hair from around the vertex of the scalp and recession of the frontal scalp margin on each side of the forehead, a process that had started in high school. The subject applied the promoter 3 to 4 times a week and after two weeks saw some fine, light colored hairs, starting to fill in along his existing hair line. With continued application for two months, the first growth of hair was about 1 inch long. New hairs coming in were dark brown and thicker. The subject has continued treatment without hair loss and with continued filling of the bald area.

EXAMPLE 4

An 86 year old female applied a promoter as in Example 1 once a week to her scalp in an amount sufficient to dampen the scalp. After several weeks she reported that her hair was thicker and fuller than it had been in years and her dandruff had disappeared.

In view of the above, it will be seen that the several objects of the invention are achieved and other advantageous results attained. As various changes could be made in the above compositions and methods without departing from the scope of the invention, it is intended that all matter contained in the above description shall be interpreted as illustrative and not in a limiting sense.

What is claimed:

1. A method of applying a hair treatment solution, the method comprising the step of applying the hair treatment solution to a scalp treatment area in sufficient quantity to wet the scalp, wherein the hair treatment solution comprises a blend of colloidal silver, colloidal copper and colloidal gold formed electrically by passing an electircal current through water between silver, copper and gold electrodes.

2. The method of claim 1 wherein the applying step includes applying the hair treatment solution in discrete treatments, each discrete treatment including an application of sufficient treatment solution to the treatment area to wet the scalp.

3. The method of claim 2 wherein the applying step includes applying the hair treatment solution in discrete treatments, the discrete treatments having a frequency of at least one time a week.

* * * * *